Figure 1:
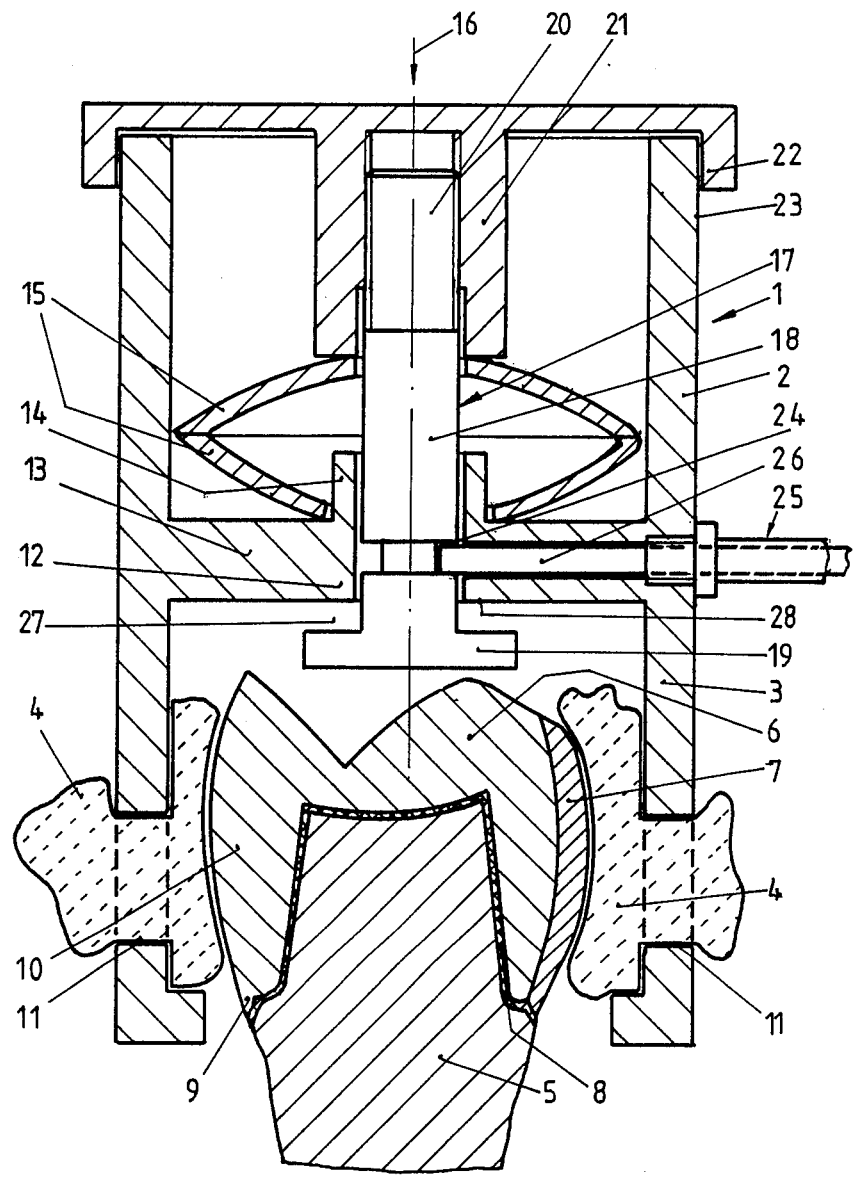

United States Patent [19]
Planert

[11] Patent Number: 4,725,233
[45] Date of Patent: Feb. 16, 1988

[54] DEVICE FOR REMOVING CROWNS, BRIDGES, AND SIMILAR STRUCTURES FROM THE STUMPS OF TEETH

[76] Inventor: Jens Planert, Friedhofsweg 1, 3402 Dransfeld, Fed. Rep. of Germany

[21] Appl. No.: 913,675
[22] PCT Filed: Oct. 30, 1985
[86] PCT No.: PCT/EP85/00577
 § 371 Date: Sep. 3, 1986
 § 102(e) Date: Sep. 3, 1986
[87] PCT Pub. No.: WO87/02573
 PCT Pub. Date: May 7, 1987

[51] Int. Cl.$^4$ .............................................. A61C 3/08
[52] U.S. Cl. ................................... 433/151; 433/120; 433/150; 433/153
[58] Field of Search ............... 433/151, 150, 153, 154, 433/156, 157, 158, 161, 162, 120, 121

[56] References Cited

U.S. PATENT DOCUMENTS

| | | | |
|---|---|---|---|
| 152,391 | 6/1874 | Manson | 433/120 |
| 394,464 | 12/1888 | Custer | 433/120 |
| 2,337,971 | 12/1943 | Caviglia | 433/151 |
| 2,376,187 | 5/1945 | Reiter | 433/151 |
| 2,776,490 | 1/1957 | Carfagni | 433/151 |
| 2,848,812 | 8/1958 | Fuest | 433/151 |
| 3,254,412 | 6/1966 | Armao | 433/151 |
| 3,553,841 | 1/1971 | Austin | 433/120 |
| 3,690,007 | 9/1972 | Curtis | 433/158 |
| 3,889,376 | 6/1975 | Zatkin | 433/161 |
| 4,300,885 | 11/1981 | Khait | 433/151 |

Primary Examiner—John J. Wilson
Attorney, Agent, or Firm—Max Fogiel

[57] ABSTRACT

A device for removing crowns, bridges, or similar structures from the stumps (5) of teeth by breaking up the cement that secures them and having an extraction frame (3) with two mutually opposed jaws (4) that engage the vicinity of the crown (6), bridge, or other structure. A mechanism (1) for applying and extracting force to the extraction frame in a direction opposite the direction (6) of insertion is provided. The mechanism (1) has a massive movable projectile (17) guided along a path that at least terminates contrary to the direction (16) of insertion and subject to a source of power that can be released. An anvil (28) is positioned at the end of the path and secured to the extraction frame (3) and to the jaws (4). The jaws (4) are designed to engage the surface (10) of the crown (6), bridge, or other structure.

10 Claims, 4 Drawing Figures

DEVICE FOR REMOVING CROWNS, BRIDGES, AND SIMILAR STRUCTURES FROM THE STUMPS OF TEETH

The invention relates to a device with the characteristics recited in the preamble to claim 1. The device is accordingly employed to remove crowns, overlays, bridges, etc. secured with cement to the stumps of one or more teeth.

A device of this type is known from U.S. Pat. No. 3,889,376. Two opposing jaws are positioned in an extraction frame and are designed and intended to act on the surface of the crown, bridge, or other structure in such a way as to gently remove it from the stump. The device also includes a mechanism for applying an extracting force to the extraction frame in a direction opposite the one that the device is inserted in. The mechanism consists of a bridge that spans the jaws and of a screw that can be screwed into a thread in the bridge. To remove the crown it is necessary to drill through it first to allow the screw to rest against the stump when the extracting force is applied. This damages the crown, which cannot be employed again. The jaws consist at least partly of rapidly hardening plastic that adapts to the surface of the crown.

A device with two jaws suspended on parallel axes of rotation in an extraction frame and capable of being pivoted toward or away from each other is known from page 66 of the periodical ZWR 11 (1980). Using the device presupposes that the jaws will catch or can be engaged beneath a projecting edge of the crown. The motion of the jaws can generally be counteracted or eliminated with a nut to prevent them from coming loose from the crown that is to be removed. This device as well can only be employed in conjunction with drilling a hole through the masticatory surface of the bridge for a spindle to rest against the stump through. The spindle is secured in the extraction frame by means of a thread. A sort of ratcheted wrench is employed to apply the requisite extracting force by twisting the spindle in relation to the extraction frame. The force develops over the thread very slowly, however, which is a drawback because the only way to release the crown is to break up the cement that attaches it or to overcome the force of the cement. Furthermore, this known device can often not be employed at the side of the oral cavity because the ratcheted wrench takes up a lot of space vertically when applied to the spindle. There must also be a lot of space available for rotating the wrench. There are various embodiments of the jaws to allow adaptation to various types of crowns, bridges, etc. Using this device presupposes that the crown has a projecting edge and accordingly differs in design from that demanded in contemporary dentistry. When the stumps of the teeth are prepared to below the edge of the gums, the gum must be forced away, especially to make it possible to apply the jaws, which is especially hard on the sleeve of the neck of the tooth and can eventually lead to the loss of the stump. This known device does, however, entail the advantage that the force that is employed is already oriented against the direction that the crown, bridge, etc. is inserted in, assuming that the jaws allow engagement in a position or at an angle corresponding to the direction of insertion.

Another device, known from U.S. Pat. No. 3,690,007 consists essentially of two jaws that are connected to each other in such a way that they can be pivoted, enabling them to be positioned together at the bridge or between two tooth stumps being spanned by the bridge. In the operating position the motion of the jaws can be restricted or blocked by a screw. One of the jaws has a perforation that a conventional crown remover, especially one in the known shape of a shepherd's crook, can be inserted into. Attempts can then be made to remove the crown, bridge, or similar structure by hammering on the other end of the crook. This device is practically impossible to use in the distal area of the rows of teeth due to its overall height. It also demands considerable skill to use. Even so, there is still a danger that the applied force will not be exerted on the bridge in opposition to the direction of insertion. Still, using a hammer makes it possible to attain a brief exertion of force sufficient to overcome the resistance of the cement.

Conventional crown removers, especially those in the known shape of a shepherd's crook, come in various embodiments. The crook is generally a rod about 25 cm long with a small, bent, spade-shaped point. The point is employed in an attempt to obtain a hold below the edges of the crown, removal knobs, intermediate bridge structures, and other areas that provide a purchase, presupposing that the crown, bridge, or other structure is appropriately designed. The other end of the crook permits carrying out an impact in the removal direction with a lead hammer. To ensure proper application of the crook, the operating end must be manually secured by the operator, with his other hand constituting a guide and abutment. An assistant, without whose help the operation can usually not be performed, uses the hammer to apply the requisite impact. The impact is extensively damped by the operator's hands and by the design-dictated resilience of the crook. Thus, the steep pulse edge of the stroke, which is important for breaking up the cement, is disadvantageously damped. Since the lead hammer has a relatively high mass in undesirable relation to the relatively small mass of the prosthesis, the stroke introduces an impact of too long a duration on the prosthesis component. Since the crook can only be grasped at one end, applying a force opposed to the direction of insertion is impossible. Engaging beneath the edges of the prosthesis entails the risk of distorting its edge, bursting any facings, which will make it impossible to reuse, at least without repair. Fracturing any projections on the stump and/or the material of the tooth itself, especially if the teeth have been root-canaled, can also occur. The extracting forces will over the course of the operation also have a deleterious effect on the periodontal retaining fibers in the plastic range. There is also a risk of damage due to the sharp edges of the mount on the crook. The edge of the crown, which always has its own particular shape, is also often damaged.

Crown-removing forceps, which differ somewhat from extractions forceps, are also known, from U.S. Pat. No. 3,834,026 for example. The drawback to using forceps of this type is that they involve a correspondingly longer lever arm and the resulting force has a long-term effect. Not only an axial force but also a torque is often simultaneously exerted on the prothesis. In extreme applications there is even a risk of unintentionally extracting the stump of the tooth itself.

The object of the invention is to provide a device of the type initially described that will make it possible to remove crown, bridge, or other dental prostheses from the stumps of teeth by breaking up the cement, specifically by means of a brief impact contrary to the direction that the prosthesis is inserted in. Neither the stump of the tooth nor the prothesis itself is to be damaged but will be available for reuse. It is especially important to tear apart the film of cement by means of a brief and powerful impulse without exerting any continuous tension on the periodontal retaining fibers.

This object is attained in accordance with the invention in that the mechanism that exerts the extracting force accommodates a massive movable projectile guided along a path that at least terminates contrary to the direction of insertion and subject to a source of power that can be released and in that an anvil is positioned at the end of the path and secured to the extraction frame and to the jaws. The mass of the projectile, which could also be called a striking pin, is relatively small and is in a practical relation to that of the dental prosthesis that is to be removed. The projectile requires only a relatively short path to position it. The path must at least terminate in a direction opposite that of insertion and can of course also parallel it over its total length. There must be an anvil at the end of the path for the projectile to impact against so that its kinetic energy will be suddenly transferred to the anvil and hence to the extraction frame and the jaws. Damping the transmission of this impulse is purposely avoided because it is essential to overcome the adhesion of the film of cement without tilting or twisting the stump. Since the prosthesis is practically not deformed and remains damaged during the extraction motion, it will be available for reuse. Use of a projectile ensures that the extracting force will act no longer than necessary on the prosthesis. Since the action occurs in the correct direction, the bridge or other structure will not bend. The risk of damage to the patient's oral cavity is also accordingly excluded. The activity of the force over time corresponds to the physiology of the retention apparatus in that a briefer and more powerful impulse tears the film of cement apart without continuous tension on the retaining fibers. The patient's subjective perception of pain is simultaneously especially limited in both intensity and time. Surprisingly, the device in accordance with the invention also makes it possible to extract a prosthesis with a ceramic or even a plastic facing. One advantage of the device is that it can be made small enough to remove distal-terminal crowns etc.

The source of power can be designed in such a way as to make it possible to vary the acceleration of the projectile. This makes it possible to exploit the dentist's skill and to adjust the power source until it is just powerful enough to ensure extraction of the prosthesis. This will considerably protect the stump's retention apparatus.

The projectile can have a bolt with a head integrated into it guided in a housing in a straight line opposite the direction of insertion and resting on a source of power in the form of a mechanical spring. A release for triggering the source of power can be provided on the bolt. The anvil can consist of a housing edge surrounding the bolt, with the head of the bolt impacting against it at the end of its path. This makes it possible to accommodate the projectile in a very small device in such a way that the impulse it supplies will act in the center of the extraction frame and specifically contrary to the direction that the prosthesis was inserted in. Distortion of the prosthesis is accordingly ruled out. The source of power can preferably be one or more cup springs, especially in the conventional package, with the capacity to apply considerable force over a short range. Since the projectile is accordingly considerably accelerated when released, the path can be relatively short, which is essential for the distal-terminal region. This design of course also makes it possible to individually adjust the tension on the package or springs in a way that is reasonable and sufficient for each case. The housing can for this purpose also be marked with a scale, making it possible to reproducibly adjust the compression of the springs and hence the release of a particular impulse. The bolt can for this purpose have a threaded shaft and an associated nut for adjusting the tension on the source of power, with the nut resting against the cup springs and the cup springs against the device's housing.

The bolt can be surrounded by a groove engaged by the release in the form of a slide. When the source of power in the form of the springs is compressed, the groove arrives in the vicinity of the release, which can then be inserted into the groove preventing initiation of motion on the part of the bolt. The release can be activated by tension or pressure like a Bowden cable or like the trigger on a camera, removing it from and releasing the groove until the projectile is accelerated by the source of power, suddenly transmitting the particular force at the end of the path. The release can naturally engage the head of the bolt instead of a groove around it.

The extraction frame that the jaws are mounted on and the housing of the mechanism for applying the extracting force can be separate parts that can be attached together. This makes it possible to employ not only different types of jaws but also different types of force-application mechanisms. Thus it will be possible to employ one mechanism with its cup springs tensioned to a prescribed degree followed by another mechanism with its cup springs tensioned to another degree. Thus, the different components of the device can easily be combined in different ways as practical and requisite for different applications. It is also possible to vary the width of the extraction frame that the jaws are mounted on or to vary the shape of the jaws in order to adapt better to a particular prosthesis. It is at an rate necessary for the jaws to engage the surface of the crown, bridge, or other structure. The jaws can also be designed or positioned to engage only the area of the prosthesis associated with one tooth in the case of two opposing sides. When the extraction frame is wider, four or six jaws, for example, can be positioned each opposite another in pairs. The jaws can also be continuous, which is a particular advantage for extracting a bridge that spans several stumps. It then also becomes possible to position either one force-application mechanism or several, distributed along the frame in such a way that the mechanisms are released in common, lifting the bridge over its total length simultaneously. The further advantage of this embodiment is that it is unnecessary to employ an adjustable source of power because a graduated series of force-application mechanisms will be available and can be employed as desired.

The projectile in another potential embodiment of the device is a ball that travels in a tubular path with compressed air as a source of power. The anvil in this case will have a web at the end of the path. The ball can be accelerated within the path by introducing compressed air into the path. At the end of the path the ball will encounter a web on the extraction frame designed so that the air impelled by the ball can escape. The web transmits the sudden impulse to the extraction frame, which transits it in turn to the jaws. The path in this case is comparatively longer and preferably curved like a tobacco pipe, with the end extending in a direction opposite the insertion direction. This will also ensure that the force will again be transmitted to extraction frame in a direction opposite that of insertion. The release in this case is embodied in a valve that admits the compressed air into the path, which is the form of a curved tube. It is simultaneously possible to control the flow of the compressed air and hence adjust the level of force.

Figure 2:
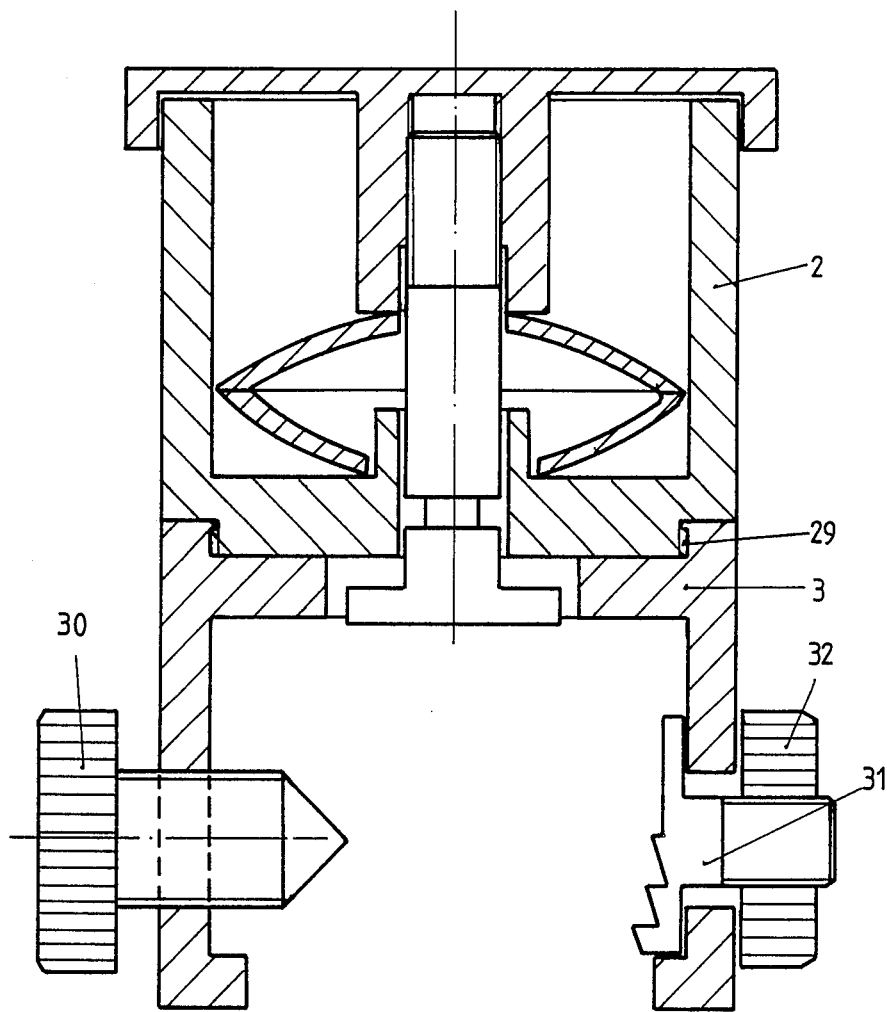
Figure 3:
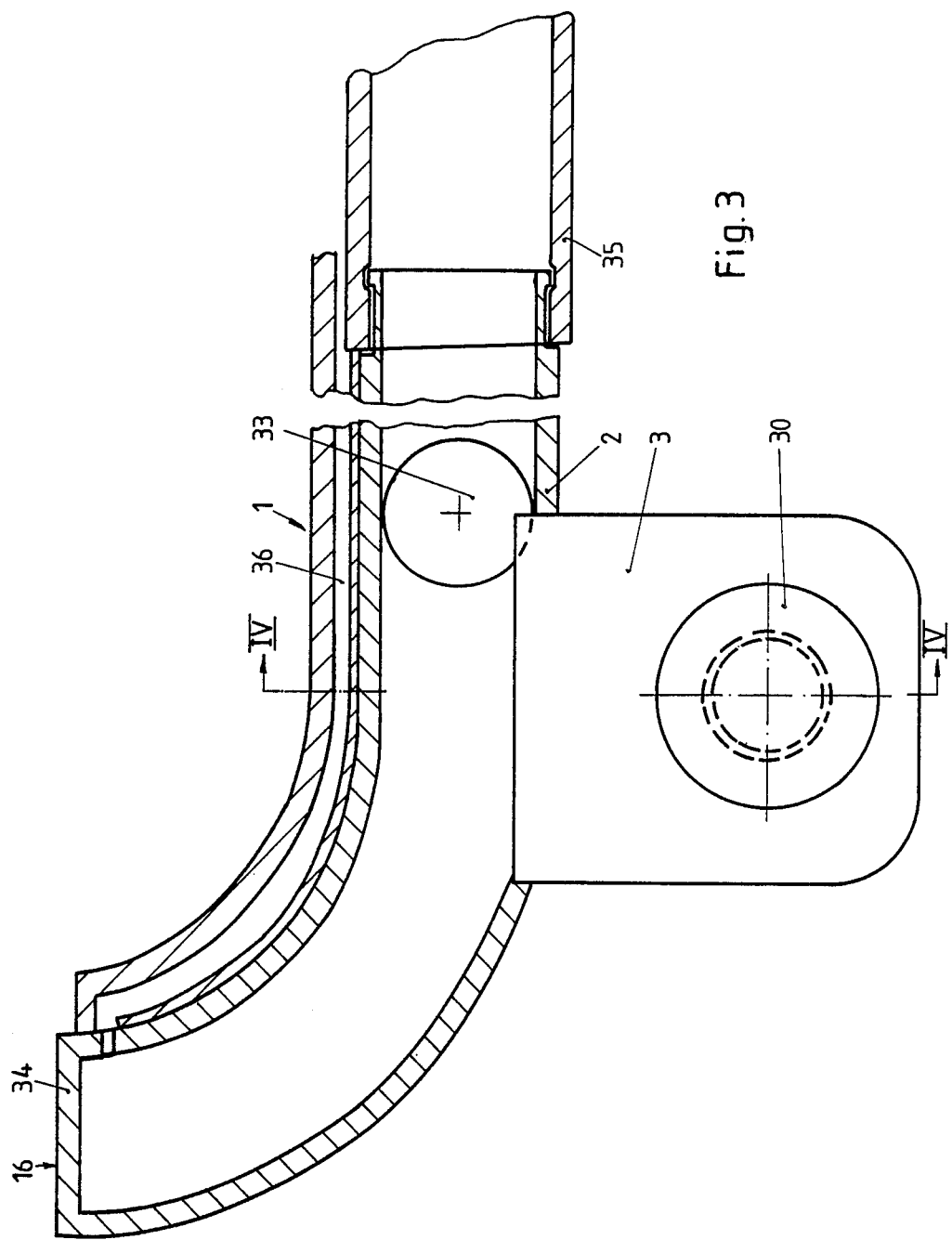
Figure 4:
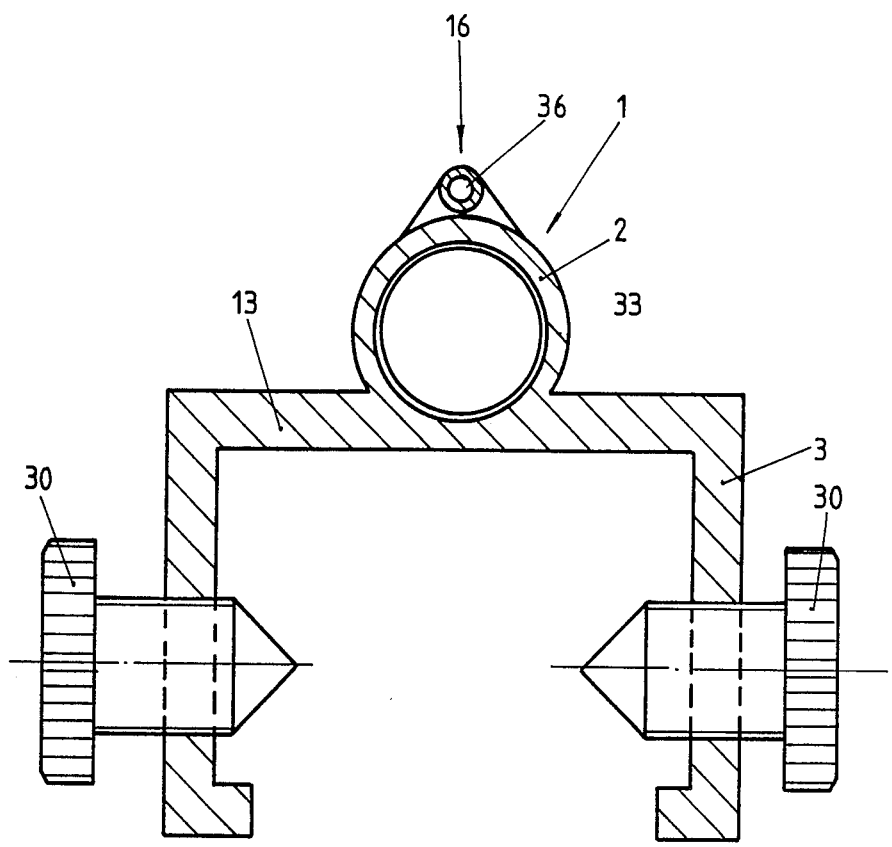

Some embodiments of the invention will now be described with reference to the drawings, wherein FIG. 1 is a vertical section through one embodiment of the device, FIG. 2 is a vertical section through another embodiment, FIG. 3 is a section through the essential components of a third embodiment, and FIG. 4 is a section along the line IV—IV in FIG. 3.

The mechanism 1 for applying an extraction force in the embodiment illustrated in FIG. 1 is mounted with its housing 2 on an extraction frame 3 or is in one piece with it. Two jaws 4 accommodated in separate wall sections are mounted on extraction frame 3. Extraction frame 3 is open at the front and rear, parallel that is to the jaw or teeth. A crown 6 and facing 7 are positioned on the stump 5 of a tooth and secured to it with a film 8 of cement. Jaws 4, as is evident, engage in the vicinity of surface 10 rather than in that of the edge 9 of crown 6 or of facing 7. Jaws 4 can in this case each consist of a mass of thermosetting plastic mounted and secured in perforations 11 through extraction frame 3.

In the vicinity of housing 2 mechanism 1 has an inwardly projecting edge 12 and a sort of false floor 13, in the vicinity of which several springs 15 in the form of cup springs are mounted by means of a collar 14.

In the center and concentric to the direction 16 of insertion, the direction, that is, that crown 6 was inserted over stump 5 in, a massive projectile 17 in the form of a bolt 18 with a head 19 is mounted in such a way that it can slide back and forth to a limited extent. Bolt 18 has a threaded shaft 20, onto which a nut 21 with a matching inside thread can be screwed to various extents. Nut 21 has a flange 22 that extends beyond housing 2. Housing 2 can have marks 23 at this point to provide a tension scale indicating how far nut 21 is screwed onto threaded shaft 20 and hence to what extent spring 15 has been tensioned. Obviously springs 15 rest against false floor 13 and on the other hand come into contact with nut 21 in such a way that projectile 17 is loaded by the resulting source of power contrary to direction 16 of insertion. Bolt 18 is surrounde by a groove 24, which is engaged by a release 25 in conjunction with a slide 26 in such a way that the components, subject to the tension of springs 15, assume the position illustrated in FIG. 1, in which the head 19 of projectile 17 is at a distance 27 from projecting edge 12. Distance 27 corresponds to the potential stroke of projectile 17 when triggered by release 25 in conjunction with slide 26, creating a path in opposition to direction 16 of insertion. At the end of the path, head 19 strikes edge 12 in the form of an anvil 28, suddenly transmitting its kinetic energy to false floor 13 and hence to housing 2, extraction frame 3, and jaws 4. Release 25 can be in the form of a Bowden cable activated by either tension or pressure.

The operation of the device will now be described. To remove crown 6 it is initially necessary to heat jaws 4, by immersing them in a water bath for example, until the thermoplastic material attains the plastic state. Thus preheated, the device is inserted over crown 6 in direction 16 of insertion, with jaws 4 coming to rest against each side of surface 10 and the thermoplastic hardening once it has attained a matching shape.

A sufficient tension for removing crown 6 has already been applied to springs 15 by rotating nut 21 in relation to threaded shaft 20 and the slide 26 on release 25 has been introduced into groove 24 by forcing nut 21 down parallel to direction 16 of insertion, so that the components assume the relative position illustrated in FIG. 1. These adjustments are made of course while the device is still outside the mouth.

Once the thermoplastic material of jaws 4 has hardened, release 25 is activated by extracting slide 26 from groove 24 so that the force of springs 15 can propel projectile 17 up contrary to direction 16 of insertion over the center of crown 6. Projectile 17 flies up to the end of the path of head 19 and suddenly impacts against anvil 28. This terminates the stroke of projectile 17, and its kinetic energy is finally transmitted in the form of a sudden impulse to crown 6, so that the adhesiveness of the film 8 of cement is overcome in a very brief time. This releases crown 6 from stump 5. The action of the force is very brief and employs the relatively small mass of projectile 17 contrary to direction 16 of insertion with one jaw 4 on each side of crown 6, resulting in a straight-line extracting motion in a direction opposite that of insertion.

Naturally other springs with different tension can be employed instead of springs 15 if the sudden impulse that is to be transmitted must be adapted to other conditions. This is the case when the area of one spring covered by marks 23 is insufficient. It should also be understood that it is possible to attach nut 21 to threaded shaft 20 in such a way that it finally cannot rotate on it, in which case the device will not be adjustable in terms of the applicable source of power but will always reproducibly exhibit and deliver the same tension. In this case it is possible to manufacture and employ devices with sources of power that differ in strength, each to be employed in accordance with the particular application.

FIG. 2 illustrates a device that, although very similar in principle, is in horizontal sections, meaning that housing 2 and extraction frame 3 do not constitute a single integrated component but can be fastened together by means of a thread 29. This ensures that various mechanisms 1 can be combined with various extraction frames 3 as desired. The intention is in particular to provide an extraction frame 3 that is not so small that it can only be employed in association with one tooth. When a bridge that spans several teeth is to be removed, extraction frame 3 can be correspondingly wide or long, with a series of pairs of jaws 4. Jaws 4 can consist of thermoplastic material (FIG. 1) or be in the form of knurled screws 30 or even sections 31 (FIG. 2). When the embodiment is composite, it is possible to secure the components together by means other than a thread 29. The idea of a plug-in connection will also occur to one skilled in the art, specifically of the type in which extraction frame 3 extends over the length of three conceivable adjacent stumps, whereas only two mechanisms 1 for example can be mounted on its top, enough to ensure uniform distribution of the extracting force over the length of the frame. Thus, the different variations have been intimated.

Jaws 4 can also be designed differently. It is possible to provide perforations 11 with appropriate threads to allow knurled screws 30 to be screwed in to an equivalent extent. Naturally, corresponding depressions must be provided on crown 6 to make it possible to transmit the requisite extracting force. These depressions, however, will not be in the vicinity of edge 9 but also in the vicinity of surface 10. A section 31 can also be secured in perforations 11 by means of check nut 32 and emplaced and positioned variously inside perforation 16.

The device illustrated in FIG. 2 functions like that illustrated in FIG. 1.

FIGS. 3 and 4 illustrate still another embodiment. Extraction frame 3 is illustrated in a side view, and the top view of knurled screw 30 shows the position of the jaws 4 constituted thereby. The housing 2 for mechanism 1 consists essentially of a pipe-like tube, within which a projectile 17 in the form of a ball 33 can slide back and forth within certain limits. The path corresponds to the curve in the tube or housing and terminates contrary to direction 16 of insertion. Anvil 28 consists of a web 34 containing several openings to allow the air pushed along by ball 33 in housing 2 to escape. Compressed air can be directed as desired against ball 33 through a connection 35 and through an unillustrated valve, accelerating the ball and finally transmitting its kinetic energy to web 34. In this case as well the energy in question is transmitted suddenly in a direction opposite direction 16 of insertion. Naturally, the end of the pipe-shaped path and hence web 34 do not absolutely have to be displaced or even should be displaced from the midline of knurled screw 30 but can in a practical way merge with it in order to distribute the transmitted impact force effectively over the crown 6 that is to be removed. A slight displacement will do no harm because the device will after all be secured by the operator. This will avoid tipping in this case as well, and hence damage to the dental prosthesis. The device can have another compressed-air line 36 in the vicinity of housing 2 and emptying in the vicinity of the web 34 in the path of ball 33 to return the ball to its rest position, at much less pressure of course. The two compressed-air lines can be activated alternately or otherwise.

I claim:

1. A device for removing elements in form of crowns, bridges and similar dental structures from stumps of teeth by breaking up cement securing said elements to the stumps, comprising: an extraction frame insertable fully into the mouth of a person having one of said elements to be removed from a stump with an axis; two mutually opposite jaws on said extraction frame for engaging a surface of said element; force applying means in said extraction frame for applying an extracting force to said extracting frame in an extracting direction opposite to direction of insertion of said element onto said stump; movable projectile means in said force applying means and guided along a predetermined path through a predetermined distance opposite to said extracting direction, said predetermined distance having an end position; a source of power within said frame for actuating said projectile means; means for releasing said source of power; abutment means fixed to said extraction frame and thereby to said jaws, said projectile means striking against said abutment means at the end of said predetermined distance and applying an extracting force directed parallel to said axis of the stump and opposite to said direction of insertion for removing said element from said stump; said extracting force being free of any force component directed at an angle inclined to said axis of said stump to prevent tipping and bending forces from being applied to the stump so that damage to the stump is prevented; said jaws being substantially fixed against motion with respect to said frame so that said frame together with said two mutually opposite jaws remain substantially stationary when said projectile means strikes said abutment means after having moved to the end of said predetermined distance, said extracting force breaking said cement only without moving substantially said element by a force impulse produced when said projectile means strikes said abutment means said extracting force being less than the force required to remove said stump.

2. A device as defined in claim 1, wherein said source of power can vary acceleration of said projectile means.

3. A device as defined in claim 1, wherein said projectile means comprises a ball traveling within a tubular path, said source of power comprising a source of compressed air applied to said ball; said abutment means having a web at the end of said predetermined distance.

4. A device as defined in claim 1, including a common extraction frame holding a plurality of pairs of jaws, at least one of said force applying means being slidable together with said extracting frame onto said common extraction frame.

5. A device as defined in claim 4, wherein each extraction frame within said common frame has separate release means for releasing said source of power, all said separate release means being simultaneously actuatable.

6. A device for removing elements in form of crowns, bridges and similar dental structures from stumps of teeth by breaking up cement securing said elements to the stumps, comprising: an extraction frame insertable fully into the mouth of a person having one of said elements to be removed from a stump with an axis; two mutually opposite jaws on said extraction frame for engaging a surface of said element; force applying means in said extraction frame for applying an extracting force to said extracting frame in an extracting direction opposite to direction of insertion of said element onto said stump; movable projectile means in said force applying means and guided along a predetermined path through a predetermined distance opposite to said extracting direction, said predetermined distance having an end position; a source of power within said frame for actuating said projectile means; means for releasing said source of power; abutment means fixed to said extraction frame and thereby to said jaws, said projectile means striking against said abutment means at the end of said predetermined distance and applying an extracting force directed parallel to said axis of the stump and opposite to said direction of insertion for removing said element from said stump; said extracting force being free of any force component directed at an angle inclined to said axis of said stump to prevent tipping and bending forces from being applied to the stump so that damage to the stump is prevented; said projectile means comprising a bolt with a head integral therewith; a housing for guiding said bolt in a substantially straight line opposite to said direction of insertion and resting on said source of power; said source of power comprising mechanical spring means; said means for releasing said source of power engaging said bolt; said abutment means comprising a housing edge surrounding said bolt.

7. A device as defined in claim 6, wherein said bolt has a threaded shaft and an associated nut for adjusting tension of said spring means.

8. A device as defined in claim 6, wherein said means for releasing said source of power has a slide, said bolt having a groove surrounding said bolt and being engaged by said slide.

9. A device as defined in claim 6, wherein said extraction frame mounting said jaws and said housing comprise separate parts that can be attached together.

10. A device for removing elements in form of crowns, bridges and similar dental structures from stumps of teeth by breaking up cement securing said elements to the stumps, comprising: an extraction frame insertable fully into the mouth of a person having one of said elements to be removed from a stump with an axis; two mutually opposite jaws on said extraction frame for engaging a surface of said element; force applying means in said extraction frame for applying an extracting force to said extracting frame in an extracting direction opposite to direction of insertion of said element onto said stump; movable projectile means in said force applying means and guided along a predetermined path through a predetermined distance opposite to said extracting direction, said predetermined distance having an end position; a source of power within said frame for actuating said projectile means; means for releasing said source of power; abutment means fixed to said extraction frame and thereby to said jaws, said projectile means striking against said abutment means at the end of said predetermined distance and applying an extracting force directed parallel to said axis of the stump and opposite to said direction of insertion for removing said element from said stump; said extracting force being free of any force component directed at an angle inclined to said axis of said stump to prevent tipping and bending forces from being applied to the stump so that damage to the stump is prevented; said source of power being able to vary acceleration of said projectile means; said projectile means comprising a bolt with a head integral therewith; a housing for guiding said bolt in a straight line opposite to said direction of insertion and resting on said source of power, said source of power comprising mechanical spring means; said means for releasing said source of power engaging said bolt; said abutment means comprising a housing edge surrounding said bolt; said bolt having a threaded shaft and a corresponding nut for adjusting tension of said spring means; said means for releasing said source of power having a slide engaging a groove surrounding said bolt; said extraction frame mounting said jaws and said housing comprising separate parts that can be attached together.

* * * * *